US010423768B2

(12) United States Patent
Martin Perez et al.

(10) Patent No.: US 10,423,768 B2
(45) Date of Patent: Sep. 24, 2019

(54) REAL-TIME USER AUTHENTICATION USING INTEGRATED BIOMETRIC SENSOR

(71) Applicant: Google Inc., Mountain View, CA (US)

(72) Inventors: Alberto Martin Perez, Los Altos, CA (US); Katie Leah Roberts-Hoffman, San Jose, CA (US)

(73) Assignee: GOOGLE LLC, Mountain View, CA (US)

( * ) Notice: Subject to any disclaimer, the term of this patent is extended or adjusted under 35 U.S.C. 154(b) by 158 days.

(21) Appl. No.: 15/220,891

(22) Filed: Jul. 27, 2016

(65) Prior Publication Data

US 2018/0032709 A1 Feb. 1, 2018

(51) Int. Cl.
| | |
|---|---|
| G06F 21/00 | (2013.01) |
| G06F 21/32 | (2013.01) |
| A61B 5/117 | (2016.01) |
| G06K 9/00 | (2006.01) |
| H04L 29/06 | (2006.01) |
| A61B 5/00 | (2006.01) |
| A61B 5/024 | (2006.01) |

(Continued)

(52) U.S. Cl.
CPC .............. *G06F 21/32* (2013.01); *A61B 5/117* (2013.01); *G06K 9/00362* (2013.01); *H04L 63/0861* (2013.01); *A61B 5/0062* (2013.01); *A61B 5/0245* (2013.01); *A61B 5/02416* (2013.01); *A61B 5/489* (2013.01); *H04L 63/0853* (2013.01); *H04W 12/06* (2013.01)

(58) Field of Classification Search
CPC ................ G06F 21/32; H04W 12/06
USPC ......................................... 726/19
See application file for complete search history.

(56) References Cited

U.S. PATENT DOCUMENTS

| | | | | |
|---|---|---|---|---|
| 5,229,764 | A | * | 7/1993 | Matchett ............ G07C 9/00158 340/5.52 |
| 7,171,680 | B2 | | 1/2007 | Lange et al. |
| 9,160,730 | B2 | * | 10/2015 | Sheller .................... H04L 63/08 |

(Continued)

OTHER PUBLICATIONS

Jorgensen, Zach, and Ting Yu. "On mouse dynamics as a behavioral biometric for authentication." Proceedings of the 6th ACM Symposium on Information, Computer and Communications Security. ACM, 2011.*

(Continued)

*Primary Examiner* — Syed A Zaidi
(74) *Attorney, Agent, or Firm* — Brake Hughes Bellermann LLP

(57) ABSTRACT

A computing device includes a housing, a processor, memory, a human interface device (i.e., a keyboard or a trackpad), and a biometric sensor integrated into the housing. The biometric sensor is configured for capturing biometric data (i.e., heartbeat data or a vein scan) from one or more of hands of a user of the device while the user's fingers are interacting with the human interface device. The memory stores executable instructions that, when executed by the at least one processor, cause the computing device to: compare the captured biometric data to one or more records of biometric data associated with the user; determine, based on the comparison, whether the captured biometric data satisfies a matching condition with the one or more records of biometric data; and authenticate the user, when the captured biometric data satisfies the matching condition.

16 Claims, 5 Drawing Sheets

(51) Int. Cl.
*A61B 5/0245* (2006.01)
*H04W 12/06* (2009.01)

(56) References Cited

U.S. PATENT DOCUMENTS

| | | | |
|---|---|---|---|
| 2009/0043216 A1 | 2/2009 | Lin et al. | |
| 2009/0150993 A1* | 6/2009 | Tilley | G06F 21/32 726/19 |
| 2010/0113950 A1 | 5/2010 | Lin et al. | |
| 2013/0051628 A1* | 2/2013 | Fukuda | G06K 9/00885 382/115 |
| 2013/0109929 A1 | 5/2013 | Menzel et al. | |
| 2013/0279768 A1* | 10/2013 | Boshra | G06F 21/32 382/124 |
| 2014/0288390 A1 | 9/2014 | Hong et al. | |
| 2015/0242605 A1* | 8/2015 | Du | G06F 21/32 726/7 |
| 2016/0142404 A1* | 5/2016 | Popovich | H04L 63/0861 726/7 |

OTHER PUBLICATIONS

Basulto, "The heartbeat vs. the fingerprint in the battle for biometric authentication", retrieved from https://www.washingtonpost.com/news/innovations/wp/2014/11/21/the-heartbeat-vs-the-fingerprint-in-the-battle-for-biometric-authentication/, Nov. 21, 2014, 3 pages.
Bollinson, "Barclays to introduce 'finger-vein ID' readers", retrieved from https://www.theguardian.com/business/2014/sep/05/barclays-introduce-finger-vein-id-readers, Sep. 5, 2014, 2 pages.
Li, et al., "Verification Based ECG Biometrics With Cardiac Irregular Conditions Using Heartbeat Level and Segment Level Information Fusion", 2014 IEEE International Conference on Acoustic, Speech and Signal Processing (ICASSP), 2014, pp. 3769-3773.
Whitehead, "Your Heart Beat Will Now Identify You for Secure Credit Card Use", retreived from https://www.mainstreet.com/article/your-heart-beat-will-now-identify-you-for-secure-credit-card-use, Mar. 24, 2015, 6 pages.
Wisniewski, "Bionym Wristband Authenticates Using Wearer's Heartbeat", retrieved from http://www.americanbanker.com/issues/178_170/bionym-wristband-authenticates-using-wearers-heartbeat-1061741-1.html, Sep. 3, 2013, 2 pages.
International Search Report and Written Opinion for PCT Application No. PCT/US2017/043701, dated Sep. 14, 2017, 14 Pages.
Rasmussen, et al., "Authentication using pulse-response biometrics", Communications of the ACM, Feb. 26, 2014, 14 Pages.

* cited by examiner

REAL-TIME USER AUTHENTICATION USING INTEGRATED BIOMETRIC SENSOR

TECHNICAL FIELD

This description generally relates to authentication of users of computing devices. The description, in particular, relates real-time user authentication through biometric data collected by a biometric sensor integrated with a computing device.

BACKGROUND

Authentication of a user of a computing device can be important to maintain the integrity, security, and privacy of information stored on, and communicated by, the computing device. Generally, users are prompted to provide authenticating information (e.g., a password, a PIN, etc.) before the user can log on to the computing device, can unlock the computing device, can access a user account through the computing device, or otherwise can make the computing device available for user by the user. However, once the proper authenticating information has been provided, the user, or different user with, or without, permission of the user, generally can continue to use the computing device without having to re-provide authentication information, unless a threshold period of inactive time is exceeded and the device become locked.

SUMMARY

In a first aspect, a method of authenticating a user while the user is interacting with a human interface device (i.e., a keyboard or a trackpad) of a computing device includes capturing biometric data (i.e., heartbeat data or a vein scan) of the user from a biometric sensor integrated into a housing of the computing device, where the biometric sensor is integrated into the housing such that the biometric data is captured from one or more of the user's hands while the user's fingers are interacting with the human interface device of the computing device. The captured biometric data is compared to one or more records of biometric data associated with the user, and, based on the comparison, a determination is made whether the captured biometric data satisfies a matching condition with the one or more records of biometric data. When the captured biometric data satisfies the matching condition, the user is authenticated.

In another general aspect, a computing device includes a housing, a processor, memory, a human interface device (i.e., a keyboard or a trackpad), and a biometric sensor integrated into the housing. The biometric sensor is configured for capturing biometric data (i.e., heartbeat data or a vein scan) from one or more of hands of a user of the device while the user's fingers are interacting with the human interface device. The memory stores executable instructions that, when executed by the at least one processor, cause the computing device to: compare the captured biometric data to one or more records of biometric data associated with the user; determine, based on the comparison, whether the captured biometric data satisfies a matching condition with the one or more records of biometric data; and authenticate the user, when the captured biometric data satisfies the matching condition.

Implementations can include one or more of the following features, alone or in any combinations with each other. For example, the biometric sensor can be integrated into a palm rest portion of the housing of the computing device, and the biometric data can be captured from at least one palm of the user, which is in contact with the palm rest portion of the housing.

The one or more records of biometric data associated with the user can include a plurality of different records of biometric data corresponding biometric data captured from the user at different times.

The biometric data can include heartbeat data captured over a period of time, where the period of time includes a time in which the user inputs a password to the computing device.

The computing device can include a display portion and a base portion connected to the display portion via a hinge, where the human interface device is integrated into the housing of the base portion.

The user can be logged out of the computing device if the captured biometric data does not satisfy the matching condition.

A message can be sent from the computing device to another computing device, if the captured biometric data does not satisfy the matching condition, where the message indicates that the captured biometric data does not satisfy the matching condition.

A determination can be made that no biometric data is captured for a period of time that exceeds a first threshold, and, based on the determination, the user can be prompted to place a palm on a palm rest portion of the housing. A determination can be made that after the prompt to the user is made no biometric data is captured for a period of time that exceeds a second threshold, and, based on the determination the user can be logged out of the computing device.

A determination can be made that biometric data is captured continuously over a period of time that exceeds a threshold, and, based on the determination, the user can be prompted to remove the user's palms from a palm rest portion of the housing.

The details of one or more implementations are set forth in the accompanying drawings and the description below. Other features will be apparent from the description and drawings, and from the claims.

DETAILED DESCRIPTION

As described herein, a biometric sensor, which may be heartbeat monitor and/or a vein scanner can be integrated into a housing of a computing device (e.g., a laptop computing device) in such a manner that heartbeat data and/or vein patterns can be captured from a hand of a user of the computing device while the user is interacting with the device. For example, the heartbeat monitor and/or vein scanner can be integrated into a portion of the housing upon which the user's hand rests while the user is typing on a keyboard of the device or while the user is utilizing a trackpad of the computing device. Heartbeat data and/or vein images can be gathered unobtrusively while the user interacts with the device. The gathered heartbeat data and/or vein images can be used to authenticate the user of the computing device. For example, different human beings can have different characteristic heartbeat patterns and/or vein patterns, so that the gathered heartbeat/vein data can be compared to a stored heartbeat or vein pattern associated with the user. The user can be authenticated when the gathered heartbeat or vein pattern data satisfies a match condition with the start heartbeat or vein pattern associated with the user. In this manner, the user can be continuously authenticated by the computing device, while the user is otherwise interacting with the computing device.

Figure 1:
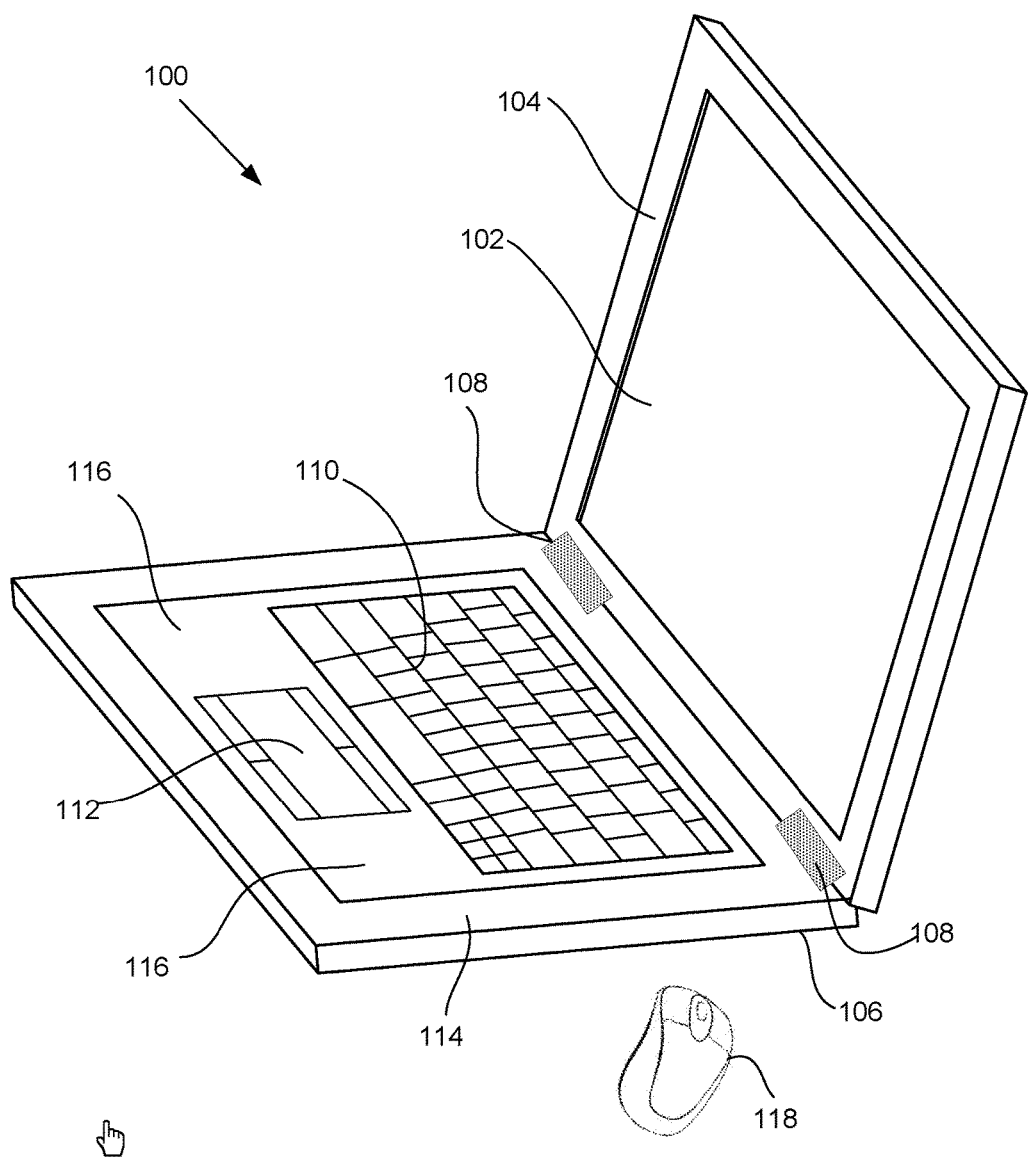
FIG. 1 is a schematic/block diagram illustrating a computing device in accordance with an example embodiment.

FIG. 1 is block diagram illustrating a computing device 100 in accordance with an example embodiment. The computing device 100 may include a heartbeat monitor and/or a vein scanner integrated in the housing of the device 100, where the heartbeat monitor is configured to capture heartbeat data and the vein scanner is configured to scan images of a user's veins from a user of the device while the device is being used by the user. As shown in FIG. 1, the computing device 100 includes a display 102 and a base portion 106, which are coupled to each other by one or more hinges 108. The display 102 may include, for example, an LCD display, and the display can include a touchscreen. The display 102 can be surrounded by a display bezel 104. The computing device 100 may include one or more human interface devices, which may include, for example, a keyboard 110, a pointing device 112, the touchscreen, and a mouse 118. The mouse 118 may communicate with a processor in the housing of the computing device 100 through a wireless connection or through a wired connection.

As shown in FIG. 1, the computing device 100 also includes a housing 114 that may be used to house various components of the computing device 100. For instance, a pointing device (e.g., a touch pad) 112 may be integrated into the housing 114. The pointing device 112 may be employed by a user of the computing device 100 to navigate the primary display 102 in order to interact with programming content that is displayed on the display 102. The keyboard 110 also can be integrated into the housing 114. The housing 114 one or more a palm-rest portions 116 into which one or more heartbeat monitors 120 and/or vein scanners 121 are integrated. The heartbeat monitors 120 and/or vein scanners 121 are shown by way of example and other arrangements are possible. For example, the housing 114 may include a single integrated heartbeat monitor scanner 120 or vein scanner 121, while in other embodiments, the housing 114 may include additional heartbeat monitors scanners 120 and/or vein scanners 121.

The palm-rest portion 116 of the housing 114 includes the portion of the housing between the keyboard 110 and the edge of the housing that is distal to the display 102 when the device 100 is in an open state when the display 102 is rotated about the hinge(s) 108 away from a configuration in which the display 102 and the base portion 106 are parallel to each other. The palm rest portion(s) 116 may include the portion of the housing 114 that is horizontally adjacent to the pointing device 112, and it may also include the pointing device itself.

In the computing device 100, the heartbeat monitor 120 and/or vein scanner 121 may be implemented in a number of fashions. For example, a heartbeat monitor 120 may include one or more exposed electrically-conductive surfaces the are electrically coupled to circuitry configured to detect and monitor electrical signals present at the surfaces. When the user's palm (i.e., any portion of the user's hand, excluding the user's fingers) is placed in contact with the electrically-conductive surface, electrical signals associated with the user's heartbeat can be detected and recorded. A pattern of recorded heartbeat signals can be associated with the user.

In other embodiments, a heartbeat monitor 120 may be implemented optically and may include a source of optical (e.g., infrared) signals that are directed into the flesh of the user's palm and a detector of optical signals that are reflected from the user's flesh. Because properties of the user's blood (e.g., density, velocity, etc.) at the location of the heartbeat monitor change during a heartbeat cycle, the detected properties of the reflected light (e.g., quantity of reflected light) that vary in accordance with the time-dependent properties of the user's blood can be used to monitor and detect the pattern of the user's heartbeat. In still other embodiments, the heartbeat monitor 120 may be implemented using other appropriate technologies, or may be implemented using a combination of different types of probes, sensors, and circuitry.

In other embodiments, a vein scanner 121 may be implemented optically and may include a source of optical (e.g., infrared) signals that are directed into the flesh of the user's palm and a detector of optical signals that are reflected from the user's flesh. The detector may include a multi-pixel detector that records images of a pattern of veins within the user's hand, where the veins are illuminated by the optical signals.

Figure 2:
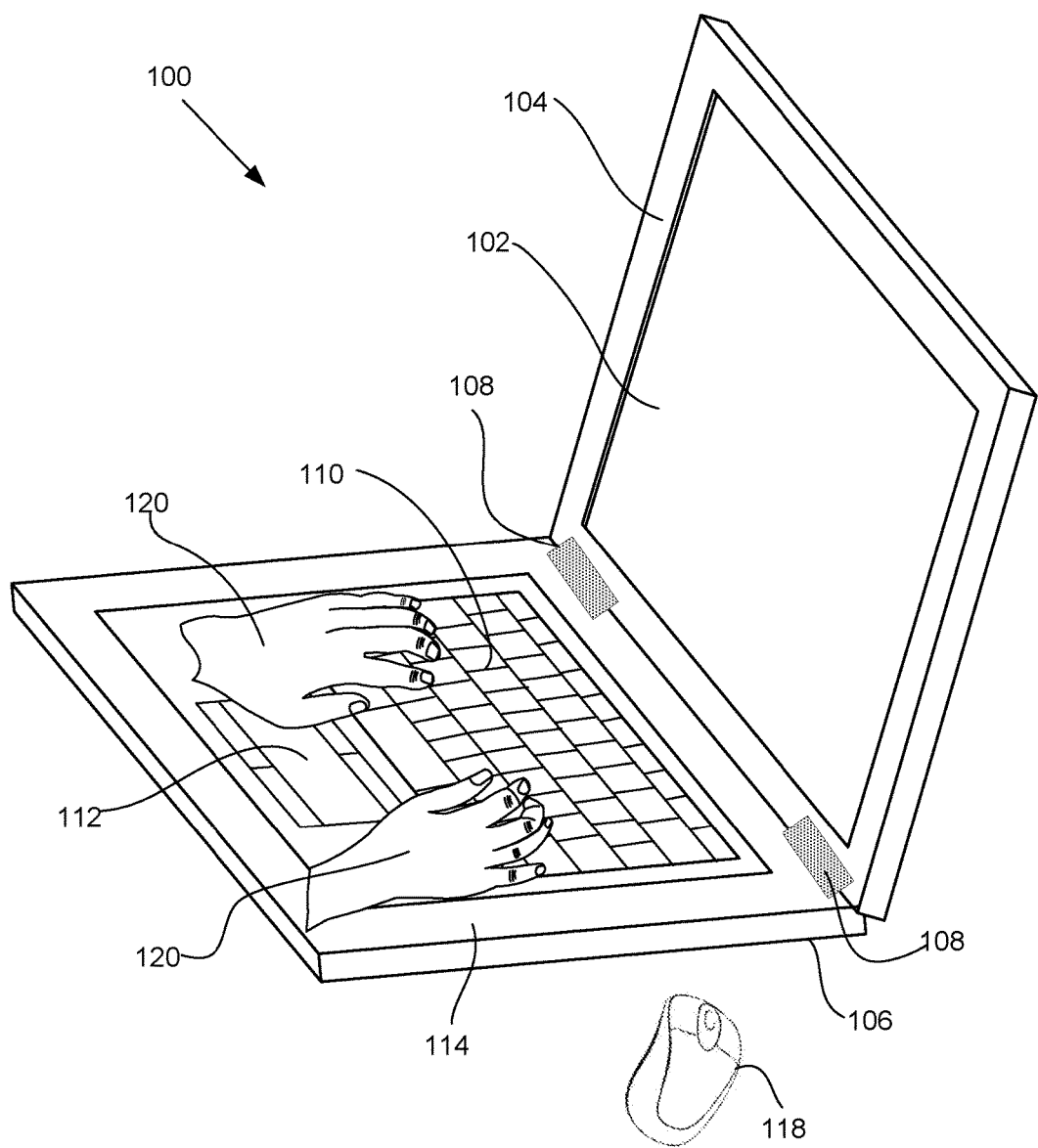
FIG. 2 is a schematic/block diagram illustrating a computing device in accordance with an example embodiment.

FIG. 2 is a schematic diagram of the computing device 100 shown in FIG. 1 in accordance with an example embodiment. The computing device 100 may correspond with the computing device 100 and include the elements of the computing device 100 described above. Accordingly, like elements in FIG. 2, as those in FIG. 1, have like reference numbers. For purposes of brevity, the like elements shown in FIGS. 1 and 2 are not be described again in detail with respect to FIG. 2.

As shown in FIG. 2, a user interacting with a human interface device (e.g., the keyboard 110 or the pointing device 112) of the device 100 can rest the palms of his or her hands 122 on palm-rest portions 116 of the housing 114 of the computing device 100. For example, while the user types on the keyboard 110, the palms of the user's hands 122 can rest on the palm-rest portions of the computing device. In this position, the heartbeat monitor 120 integrated into the housing of the computing device 100 can capture heartbeat data from the user as the user interacts with the computing device 100. In this position, the vein scanner 121 integrated into the housing of the computing device 100 can capture images of the user's veins from the user as the user interacts with the computing device 100.

Figure 3:
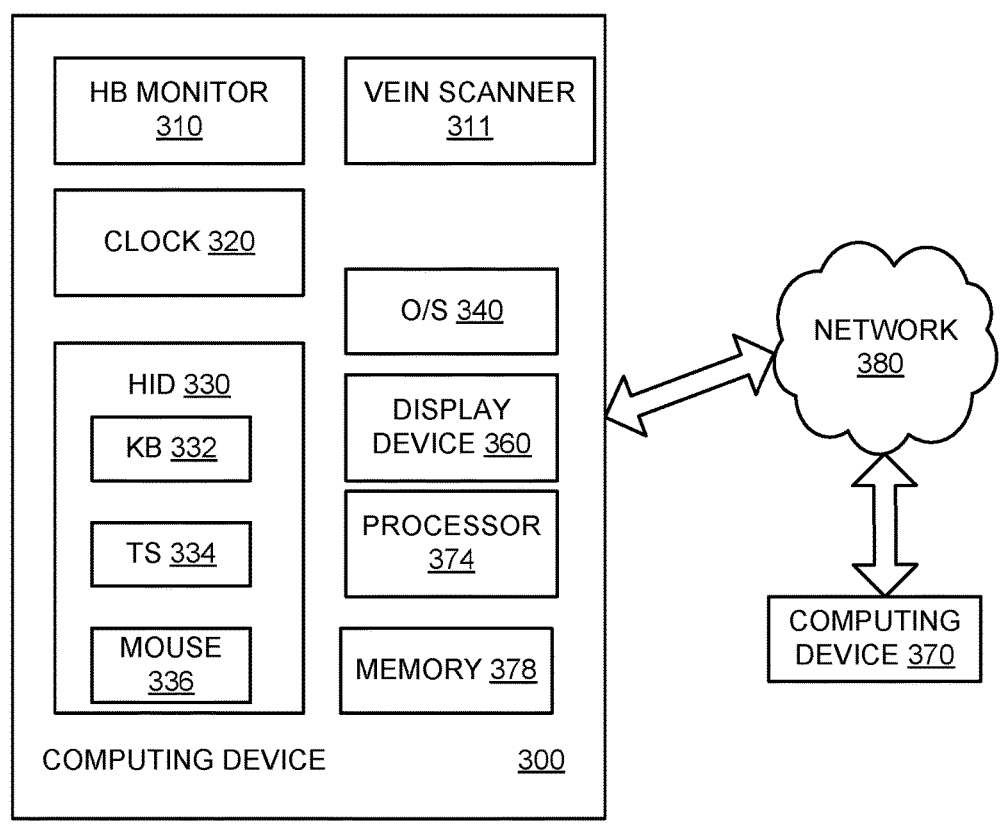
FIG. 3 is a block diagram illustrating a computing device that may be used to implement real-time authentication of a user of the computing device based on biometric data gathered from the computing device in accordance with an example embodiment.

FIG. 3 is a block diagram illustrating system 399 including a computing device 300 that may be used to gather heartbeat data from a user of the device while the user is interacting with the device in accordance with an example embodiment. As shown in FIG. 3, the computing device 300 may include one or more heartbeat monitors 310, one or more vein scanners 311, a clock 320, one or more human interface devices (e.g., a touchpad 332, a keyboard 334, a mouse 336) 330, an operating system 340, a display device 360, a processor 374 and a memory 378, which may be used, in appropriate combinations, to implement one or more user authentication based on heartbeat data and/or vein scans gathered by the heartbeat monitor 310 and/or vein scanner 311 of the computing device 300. For instance, the memory 378 may be configured to store instructions for implementing user heartbeat monitoring/vein scanning and user authentication based on the monitored heartbeat data/vein scanning on the computing device 300 and the processor 374 may be configured to execute those instructions to implement the monitoring and authentication.

It will be appreciated that the elements of the system 399 illustrated in FIG. 3 for implementing heartbeat monitoring/vein scanning and user authentication are shown by way of illustration. In other embodiments, elements for implementing heartbeat monitoring and/or vein scanning may be added to and/or eliminated from the computing device 300. For instance, the computing device 300 may include a network interface device (not shown). Such a network interface device may allow the computing device 300 to access a network 380 and to provide heartbeat/vein scan data gathered locally from the device 300 to a remote computing device 370 that can use the provided heartbeat/vein scan data to authenticate the user to the remote computing device 370, to an account associated with the remote computing device 370, etc. The network 380 may take a number of forms, such as a private network (e.g., a local area network) or a public network (e.g., the Internet).

The heartbeat monitor 310 that is integrated into a housing of the computing device 300 can be used to capture heartbeat data from a user as the user is using the computing device. For example, while the user is interacting with a human interface device 330 of the computing device 300 (e.g., one or more of the user's fingers are typing on a keyboard 334 or moving a cursor with a touch pad of the device) heartbeat data can be captured by the heartbeat monitor 310. The heartbeat data can be captured over a period of time, so that a pattern of the user's heartbeat can be determined from the gathered data. Then, the gathered data can be compared to one or more records of heartbeat data that are associated with the user. In some implementations, the records of heartbeat data can be captured and stored in memory 378 when the user the user provides explicit consent to do so, for example, after responding positively to a prompt on the display device 360 that the user has the opportunity to record heartbeat data to be used for real-time authentication of the user at a later time. Heartbeat data can be associated with a particular user, when the user links gathered heartbeat data to himself or herself, for example, by logging into an account associated with the user (e.g., a local account associated with the computing device 300 or a device-independent, cloud-based account) and then permitting the heartbeat monitor 310 to gather heartbeat data from the user.

Heartbeat data gathered by the heartbeat monitor 310 can be compared to previously gathered records of heartbeat data associated with the user. Because different people have different heartbeat patterns, the comparison of the gathered data and the previously gathered data can be used to authenticate the user when the gathered data and the previously gathered data satisfy a matching condition. For example, the gathered heartbeat data and the previously gathered heartbeat data can include patterns representing a blood pressure or voltage amplitude of the user's heart over a period of time, where the period of time includes at least one heartbeat cycle. The gathered data and the previously gathered data can be compared using a variety techniques, which may involve, for example, normalizing the data and comparing a plurality of values of the normalized heartbeat data that has been gathered to a plurality of normalized values of the previously gathered heartbeat data.

In one example technique, the two data patterns can be normalized to a common average heart rate for the two patterns and their amplitudes can be similarly normalized. Then, the absolute value of the difference in normalized amplitudes between the two patterns can be integrated over time period equal to at least a portion of one heartbeat cycle. If the value of the integral is less than a threshold value, or if the value of the value of the integral divided by the integral of one or, or the average of, the patterns over the same time period is less than a threshold value, the matching condition can be satisfied. The user can be authenticated, based on determining that the matching condition is satisfied. If the matching condition is not satisfied, a determination can be made that the user is not authenticated.

In some implementations, the gathered heartbeat data can be compared to a plurality of records of heartbeat data associated with a user. The plurality of records can include records that may be somewhat different from each other but nevertheless characteristic of the user. For example, the plurality of records can include records gathered when the user is, for example, at rest, stressed, immediately after strenuous exercise, etc. In some implementations, if a matching condition is satisfied between the gathered data and any one of the plurality of records associated with the user, the user can be authenticated. In some implementations, a user may be authenticated only if the gathered data matches a particular record. For example, if the gathered data is determined to be associated with a user at rest (e.g., if the heartrate of the data is less than a predetermined value, such as, for example, 65 beats per minute), the user may be authenticated only if the gathered heartbeat data satisfies a matching condition with a record of heartbeat data gathered with the user is at rest.

In some cases, a captured heartbeat data pattern may be insufficient to uniquely identify a particular person from all people in the world, or even even from each member of a random sample of a smaller number (e.g., 10,000) of other people. Nevertheless, a captured heartbeat data pattern may be sufficient to distinguish the user from whom the heartbeat data is captured from a random sample of a threshold number (e.g., 300) people with a threshold level of confidence (e.g., 95% confidence). In such cases, the user may authenticated based on the gathered heartbeat data when the user is distinguished from the threshold number of random people with the threshold level of confidence and the user may not be authenticated if the user is not distinguished from the threshold number of random people with the threshold level of confidence.

The vein scanner 311 that is integrated into a housing of the computing device 300 can be used to capture images of veins in the user's hand as the user is using the computing device. For example, while the user is interacting with a human interface device 330 of the computing device 300 (e.g., one or more of the user's fingers are typing on a keyboard 334 or moving a cursor with a touch pad of the device) vein images can be captured by the vein scanner 311. Then, the gathered vein images can be compared to one or more records of vein images that are associated with the user. In some implementations, the records of vein images can be captured and stored in memory 378 when the user the user provides explicit consent to do so, for example, after responding positively to a prompt on the display device 360 that the user has the opportunity to record vein images to be used for real-time authentication of the user at a later time. Vein images can be associated with a particular user, when the user links gathered vein images to himself or herself, for example, by logging into an account associated with the user (e.g., a local account associated with the computing device 300 or a device-independent, cloud-based account) and then permitting the vein scanner 311 to gather vein images from the user.

Vein images gathered by the vein scanner 311 can be compared to previously gathered records of vein images associated with the user. Because different people have different patterns of veins in their hands, as with heartbeat data, the comparison of the gathered images and the previously gathered vein images can be used to authenticate the user when the gathered vein images and the previously gathered vein images satisfy a matching condition. The user can be authenticated, based on determining that the matching condition is satisfied. If the matching condition is not satisfied, a determination can be made that the user is not authenticated.

In some cases, a captured vein images can provide a more accurate verification of a user than a heartbeat data pattern for the user. For example, while a captured heartbeat data pattern may be sufficient to distinguish the user from whom the heartbeat data is captured from a random sample of a first threshold number (e.g., 300) of people with a threshold level of confidence (e.g., 95% confidence), a captured vein image may be sufficient to distinguish the user from a random sample of a second threshold number (e.g., 100,000,000) of people that is higher than the first threshold number of people with the same threshold level of confidence (e.g., 95% confidence).

In some implementations, when the computing device includes both a heartbeat monitor 310 and a vein scanner 311, if the user fails the authentication test based on captured heartbeat data, the user may be required provide a vein scan to the vein scanner 311 to authenticate himself or herself.

In response to the determination that the user is not authenticated, or that the user fails the authentication test, one or more actions can be taken. For example, the user can be automatically logged out of the computing device 300 when the authentication fails. This can be useful for a user if the user is using the computing device 300 in a public space and a person other than the user takes possession of the computing device 300. By authenticating the user of the computing device 300 based on heartbeat data or vein scans while the user is utilizing the device, the device can be protected against unauthorized use by someone other than the user, even after the user has logged into the device.

In addition, authenticating a user based on heartbeat data or vein scans captured while the user is utilizing the device can be useful for ensuring that information provided to the computing device 300 and/or transmitted from the computing device 300 across a network to another computing device 300 is provided by, or transmitted by, the user. For example, when the computing device 300 is used in an educational environment, authenticating the user based on heartbeat data or vein scans can be used to ensure that answers to test questions provided to the computing device 300 are, in fact, provided by the user and not by another user. For example, after a user has authenticated himself or herself to the computing device 300 (e.g., by entering password credentials or by providing a vein scan through the vein scanner 311), so that test answers provided through the computing device 300 are associated with the user, authentication of the user by heartbeat data or vein scans can ensure that answers provided throughout the duration of the test are provided by the user and not by a different user of the computing device 300. If heartbeat data or vein scans captured during the test fails the matching condition, a message can be sent from the computing device 300 to another computing device 300 (e.g., the computing device 300 of a teacher) to alert a person associated with the other computing device 300 that the matching condition has not been satisfied, which may indicate that test answers have been provided fraudulently.

In addition, authenticating a user based on heartbeat data or vein scans captured while the user is utilizing the computing device 300 can be useful for validating other authentication information provided to the computing device 300. For example, when the heartbeat data or vein scan is captured while the user is typing a password on the keyboard 334, the captured heartbeat data or vein scan can be used as user-specific biometric information to validate the password provided to the computing device 300. The user may be permitted to access the computing device 300 only when both the correct password information is provided through the keyboard 334 and when the heartbeat data or vein scan captured while the user enters the password information satisfies a matching condition with a record of heartbeat data or vein scan associated with the user.

Various prompts can be sent to the user based on the heartbeat data or vein scan captured through the heartbeat monitor 310 or vein scanner 311 while the user interacts with a human interface device 330 of the computing device 300. For example, to ensure that a particular user, and not any other user, is using the device, a prompt can be sent (e.g., via the display 360) to the user to place one of his or her palms on the palm-rest portion of the housing if heartbeat data or a vein scan has not been captured from the integrated heartbeat monitor 310 or vein scanner 311 for more than a threshold period of time while the device has been in use (e.g., while input to the device has been received through the touchscreen, through voice commands, through keyboard input provided without the palms of the user being in contact with the integrated heartbeat monitor 310 or vein scanner 311, etc.), so that heartbeat data or a vein scan can be captured from the user of the device and used to authenticate the user of the device via heartbeat data or a vein scan. In some implementations, if the user does not place a hand in contact with a heartbeat monitor or a vein scanner, and a determination is made that no heartbeat data and no vein scan is received, within a threshold time period after the prompt, the user can be automatically logged off of the computing device.

In another example, to assist a user with preventing repetitive strain injury, a prompt can be sent to the user when heartbeat data associated with a user has been captured continuously from the integrated heartbeat monitor 310 for more than a threshold period of time (e.g., 20 minutes), or when heartbeat data is captured during more than a threshold percentage of time during a predetermined period of time (e.g., 95% of one hour). The prompt can suggest that the user temporarily remove his or her hands from the human interface device 330 to prevent repetitive strain injury.

The computing device 300 can include a plurality of heartbeat monitors 310 configured to capture heartbeat data from the user and a plurality of vein scanner 311 configured to capture vein scans from the user. For example, the housing of the computing device can include left and right heartbeat monitors 310 or vein scanners 311 integrated into left and right palm-rest portions of the housing of the computing device 300, and the mouse 336 also can include a heartbeat monitor or vein scanner integrated into a housing of the mouse 336. Heartbeat data and vein scans can be captured from all of the heartbeat monitors 310 and vein scans and used collectively to authenticate the user of the computing device 300. For example, heartbeat data gathered from the different heartbeat monitors 310 can be synchronized, e.g., based on a timing signal from the clock 320. Therefore, a pattern of heartbeat data can be gathered from the different heartbeat monitors over a time interval, even if the user removes a hand from one heartbeat monitor, so long as at least the user maintains contact with at least one of the plurality of heartbeat monitors 310 during the time interval.

Figure 4:
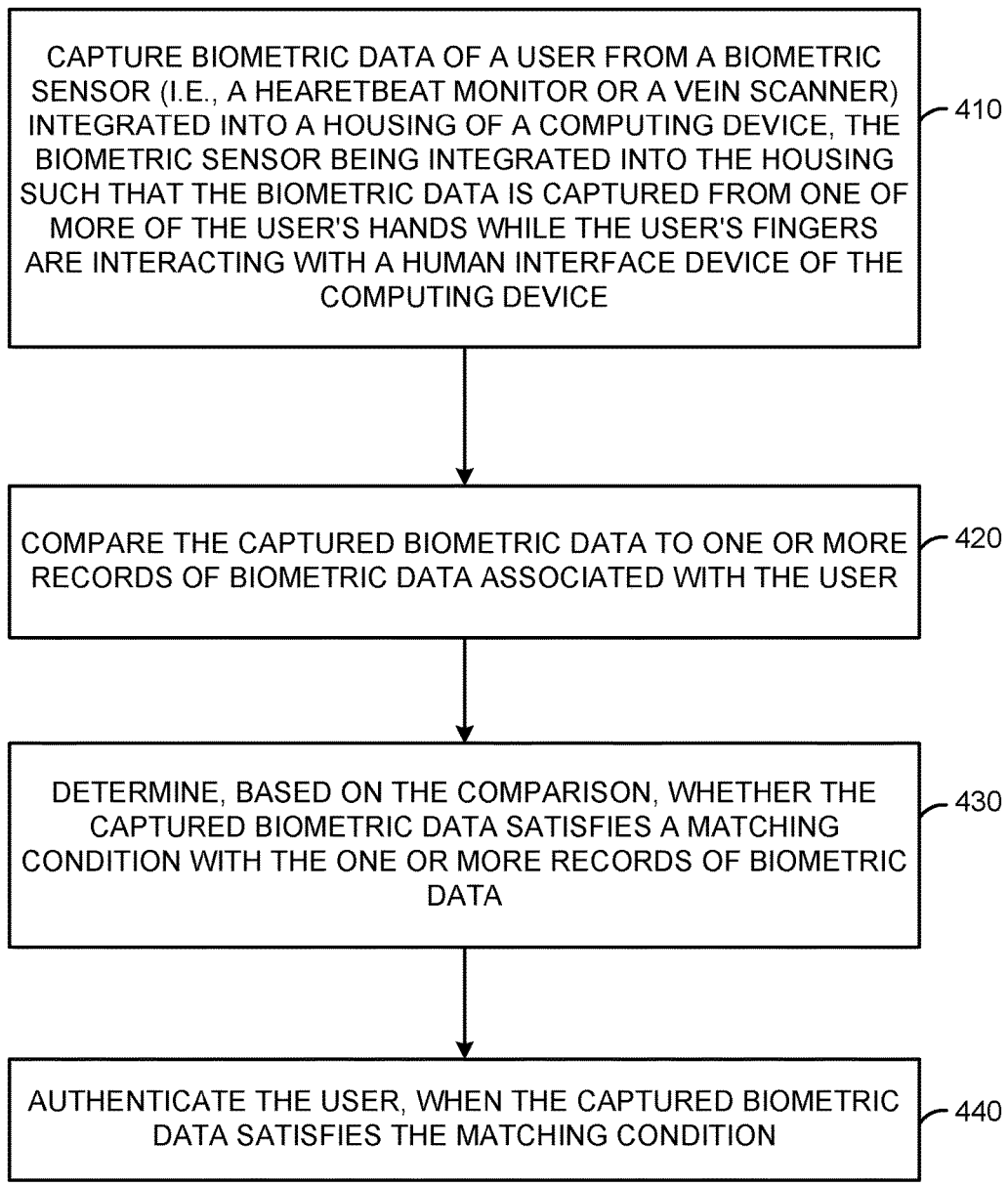
FIG. 4 is a flowchart illustrating a method in accordance with an example embodiment.

FIG. 4 is a flowchart illustrating a method for authenticating a user of a computing device while the user is interacting with a human input device of the computing device. The method 400 may be implemented, for example, using the approaches described herein. For instance, the method 400 may be implemented using the computing devices illustrated and described with respect to FIGS. 1-3.

The method 400 includes, at block 410, capturing biometric data of the user from a biometric sensor (i.e., a heartbeat monitor or a vein scanner) integrated into a housing of the computing device. The biometric sensor is integrated into the housing such that the biometric data is captured from one or more of the user's hands while the user's fingers are interacting with the human interface device of the computing device, and the human interface device is either a keyboard or a trackpad. The method 400 further includes, at block 420, comparing the captured biometric data to one or more records of biometric data associated with the user. The method 400 also includes, at block 430, determining, based on the comparison, whether the captured biometric data satisfies a matching condition with the one or more records of biometric data. The method 400 still further includes, at block 440, authenticating the user, when the captured biometric data satisfies the matching condition.

Although the techniques described herein have been described in relation to the computing devices described above and in FIGS. 1-4, other implementations are also possible. For example, the computing device can be a desktop or server computing device having a keyboard that is detached from the chassis that houses the processor and memory of the computing device, and the housing of the computing device into which the biometric sensor is integrated can be the housing of the keyboard. In another implementation, the housing of the computing device into which the biometric sensor is integrated can be the housing of the mouse 336, such that biometric data is captured from the biometric sensor that is contacted by the user's hand that grasps the mouse.

Figure 5:
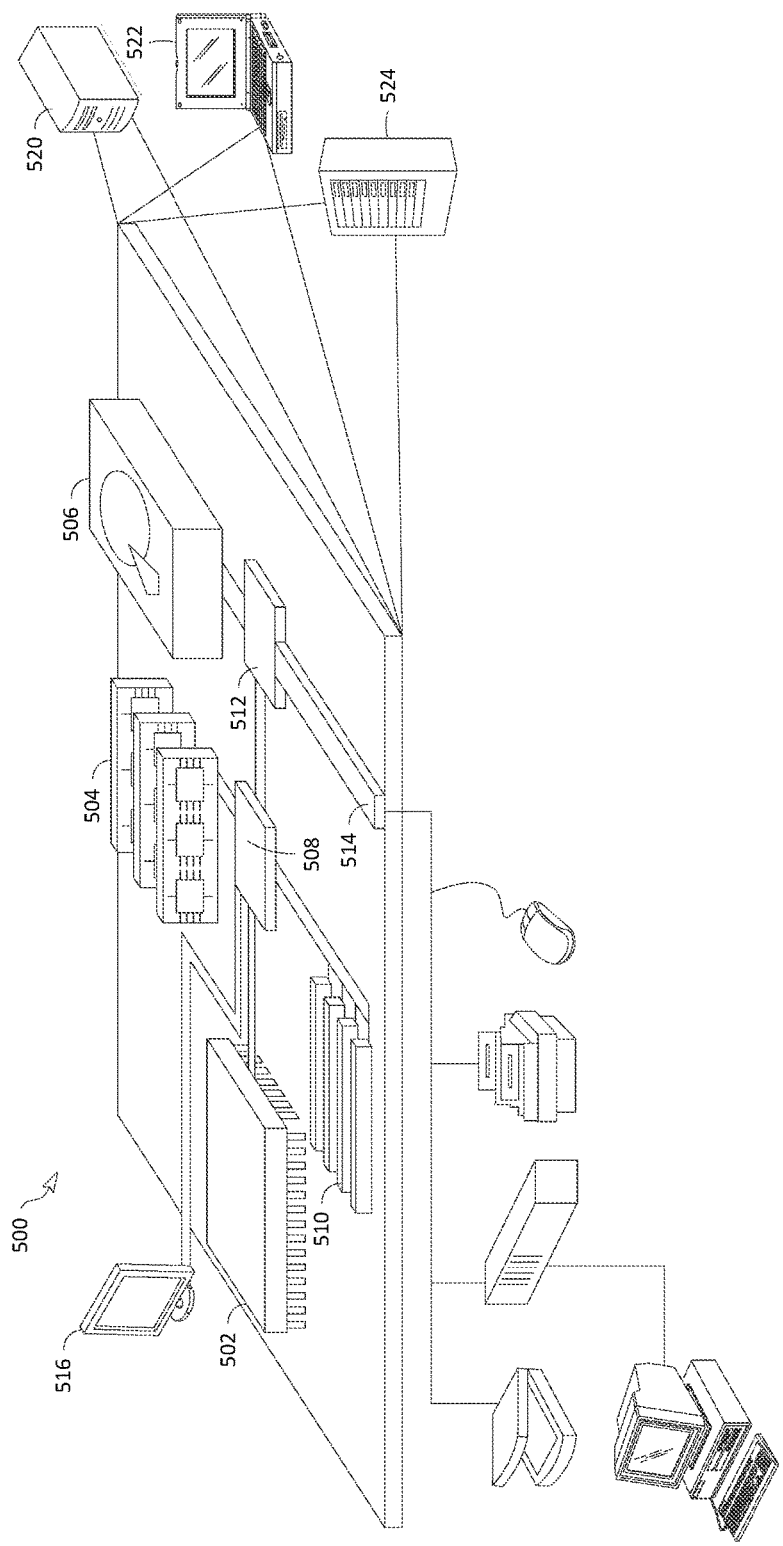
FIG. 5 is a diagram that illustrates a computing device and a mobile computing device that can be used to implement the techniques described herein in accordance with an example embodiment.

FIG. 5 shows an example of a generic computer device 500 that may be used with the techniques described here. Computing device 500 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

Computing device 500 includes a processor 502, memory 504, a storage device 506, a high-speed interface 508 connecting to memory 504 and high-speed expansion ports 510, and a low speed interface 512 connecting to low speed bus 514 and storage device 506. Each of the components 502, 504, 506, 508, 510, and 512, are interconnected using various busses, and may be mounted on a common motherboard or in other manners as appropriate. The processor 502 can process instructions for execution within the computing device 500, including instructions stored in the memory 504 or on the storage device 506 to display graphical information for a GUI on an external input/output device, such as display 516 coupled to high speed interface 508. In other implementations, multiple processors and/or multiple buses may be used, as appropriate, along with multiple memories and types of memory. Also, multiple computing devices 500 may be connected, with each device providing portions of the necessary operations (e.g., as a server bank, a group of blade servers, or a multi-processor system).

The memory 504 stores information within the computing device 500. In one implementation, the memory 504 is a volatile memory unit or units. In another implementation, the memory 504 is a non-volatile memory unit or units. The memory 504 may also be another form of computer-readable medium, such as a magnetic or optical disk.

The storage device 506 is capable of providing mass storage for the computing device 500. In one implementation, the storage device 506 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above. The information carrier is a computer- or machine-readable medium, such as the memory 504, the storage device 506, or memory on processor 502.

The high speed controller 508 manages bandwidth-intensive operations for the computing device 500, while the low speed controller 512 manages lower bandwidth-intensive operations. Such allocation of functions is exemplary only. In one implementation, the high-speed controller 508 is coupled to memory 504, display 516 (e.g., through a graphics processor or accelerator), and to high-speed expansion ports 510, which may accept various expansion cards (not shown). In the implementation, low-speed controller 512 is coupled to storage device 506 and low-speed expansion port 514. The low-speed expansion port, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. It may also be implemented as part of a rack server system 524. In addition, it may be implemented in a personal computer such as a laptop computer 522. Alternatively, components from computing device 500 may be combined with other components in a mobile device (not shown). Each of such devices may contain one or more of computing device 500 and an entire system may be made up of multiple computing devices 500 communicating with each other.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing device that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing device can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications may be made without departing from the spirit and scope of the invention.

In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

What is claimed is:

1. A method of authenticating a user while the user is interacting with a human interface device of a computing device, the method comprising:
    capturing biometric data of the user from a biometric sensor integrated into a housing of the computing device, the biometric sensor being integrated into the housing such that the biometric data is captured from one or more of the user's hands while the user's fingers are interacting with the human interface device and while entering a password to the computing device, wherein the human interface device is selected from the group consisting of a keyboard and a trackpad, wherein the biometric data is selected from the group consisting of heartbeat data and a vein scan, and wherein the biometric sensor is selected from the group consisting of a heartbeat monitor and a vein scanner;
    comparing the captured biometric data to one or more records of biometric data associated with the user;
    determining, based on the comparison, whether the captured biometric data satisfies a matching condition with the one or more records of biometric data;
    authenticating the user, when the captured biometric data satisfies the matching condition;
    determining that biometric data of the user is not captured for a first period of time that exceeds a first threshold; and
    prompting the user, based on the determining that biometric data of the user is not captured for the first period of time that exceeds the first threshold, to place the one or more of the user's hands on a palm rest portion of the housing.

2. The method of claim 1,
    wherein the biometric sensor is integrated into the palm rest portion of the housing of the computing device, and
    wherein the biometric data is captured from at least one hand of the user, which is in contact with the palm rest portion of the housing.

3. The method of claim 1, wherein the one or more records of biometric data associated with the user include a plurality of different records of biometric data corresponding to biometric data captured from the user at different times.

4. The method of claim 1, wherein the computing device includes a display portion and a base portion that are connected via a hinge and wherein the human interface device is integrated into the housing of the base portion.

5. The method of claim 1, further comprising logging the user out of the computing device if the captured biometric data does not satisfy the matching condition.

6. The method of claim 1, further comprising, sending a message from the computing device to another computing device, if the captured biometric data does not satisfy the matching condition, the message indicating that the captured biometric data does not satisfy the matching condition.

7. The method of claim 1, further comprising:
    determining that after the prompting, no biometric data is captured for a second period of time that exceeds a second threshold; and
    based on the determination, logging the user out of the computing device.

8. The method of claim 1, further comprising:
    determining that biometric data is captured continuously over a third period of time that exceeds a third threshold; and
    based on the determination, prompting the user to remove hands of the user from a palm rest portion of the housing.

9. A computing device comprising:
    a housing;
    a biometric sensor integrated into the housing and configured for capturing biometric data from one or more hands of a user of the device while the user's fingers are interacting with a human interface device of the computing device and while entering a password to the computing device, wherein the human interface device is selected from the group consisting of a keyboard and a trackpad, wherein the biometric data is selected from the group consisting of heartbeat data and a vein scan, and wherein the biometric sensor is selected from the group consisting of a heartbeat monitor and a vein scanner;

at least one processor;

memory storing executable instructions that, when executed by the at least one processor, cause the computing device to:

capture, with the biometric sensor, biometric data from one or more of hands of the user of the device while the user's fingers are interacting with the human interface and while the user enters a password to the computing device;

compare the captured biometric data to one or more records of biometric data associated with the user;

determine, based on the comparison, whether the captured biometric data satisfies a matching condition with the one or more records of biometric data;

authenticate the user, when the captured biometric data satisfies the matching condition;

determine that biometric data of the user is not captured for a first period of time that exceeds a first threshold; and prompt the user, based on the determining that biometric data of the user is not captured for the first period of time that exceeds the first threshold, to place the one or more of the user's hands on a palm rest portion of the housing.

10. The computing device of claim 9, wherein the housing includes the palm rest portion and wherein the biometric sensor is integrated into the palm rest portion of the housing and is configured to capture the biometric data from at least one hand of the user when the at least one hand is in contact with the palm rest portion of the housing.

11. The computing device of claim 9, wherein the one or more records of biometric data associated with the user include a plurality of different records of biometric data corresponding to biometric data captured from the user at different times.

12. The computing device of claim 9, further comprising:
a display portion; and
a base portion connected to the display portion via a hinge, wherein the human interface device is integrated into the housing of the base portion.

13. The computing device of claim 9, wherein the memory further stores executable instructions that, when executed by the at least one processor, cause the computing device to log the user out of the computing device if the captured biometric data does not satisfy the matching condition.

14. The computing device of claim 9, wherein the memory further stores executable instructions that, when executed by the at least one processor, cause the computing device to send a message from the computing device to another computing device, if the captured biometric data does not satisfy the matching condition, the message indicating that the captured biometric data does not satisfy the matching condition.

15. The computing device of claim 9, wherein the memory further stores executable instructions that, when executed by the at least one processor, cause the computing device to:
determine that after the prompting, no biometric data is captured for a second period of time that exceeds a second threshold; and
based on the determination, log the user out of the computing device.

16. The computing device of claim 9, wherein the memory further stores executable instructions that, when executed by the at least one processor, cause the computing device to:
determine that biometric data is captured continuously over a third period of time that exceeds a third threshold; and
based on the determination, prompt the user to remove hands of the user from a palm rest portion of the housing.

* * * * *